US008435747B2

(12) United States Patent
Hill et al.

(10) Patent No.: US 8,435,747 B2
(45) Date of Patent: May 7, 2013

(54) NON-PROTEOLYTIC METHOD FOR THE DETERMINATION OF ANALYTES IN KERATINIZED STRUCTURES

(75) Inventors: Virginia Hill, Los Angeles, CA (US); Mohammad Atefi, Los Angeles, CA (US); Michael I. Schaffer, Los Angeles, CA (US)

(73) Assignee: Psychemedics Corporation, Acton, MA (US)

( * ) Notice: Subject to any disclaimer, the term of this patent is extended or adjusted under 35 U.S.C. 154(b) by 81 days.

(21) Appl. No.: 12/990,447

(22) PCT Filed: Apr. 29, 2009

(86) PCT No.: PCT/US2009/042056
§ 371 (c)(1),
(2), (4) Date: Jan. 12, 2011

(87) PCT Pub. No.: WO2009/134852
PCT Pub. Date: Nov. 5, 2009

(65) Prior Publication Data
US 2011/0104714 A1    May 5, 2011

(51) Int. Cl.
*G01N 33/53* (2006.01)
(52) U.S. Cl.
USPC ............................................ 435/7.1; 436/518
(58) Field of Classification Search ........................ None
See application file for complete search history.

(56) References Cited

U.S. PATENT DOCUMENTS

| | | | |
|---|---|---|---|
| 4,956,467 A | 9/1990 | Hinman et al. | |
| 5,324,642 A | 6/1994 | Baumgartner | |
| 5,466,579 A | 11/1995 | Baumgartner | |
| 6,022,693 A | 2/2000 | Baumgartner | |
| 6,350,582 B1 | 2/2002 | Baumgartner | |
| 6,582,924 B1 | 6/2003 | Baumgartner | |
| 6,949,344 B1 | 9/2005 | Baumgartner | |
| 7,083,925 B2 | 8/2006 | Schnabel et al. | |
| 7,252,961 B2 | 8/2007 | Neuenhofer et al. | |
| 7,297,554 B2 | 11/2007 | Chung et al. | |
| 7,618,591 B2 | 11/2009 | Slowey et al. | |
| 7,629,129 B1 | 12/2009 | Sekowski et al. | |
| 8,084,215 B2 | 12/2011 | Hill et al. | |
| 2004/0241776 A1 | 12/2004 | Geister et al. | |
| 2009/0269791 A1 | 10/2009 | Hill et al. | |

FOREIGN PATENT DOCUMENTS

| | | |
|---|---|---|
| EP | 0 458 594 | 6/1996 |
| JP | 06-503424 | 4/1994 |
| WO | WO 99/30160 | 6/1999 |
| WO | WO 99/42838 | 8/1999 |
| WO | WO 01/84157 | 11/2001 |
| WO | WO 2006/078618 | 7/2006 |

OTHER PUBLICATIONS

Ahrens et al., "Detection of morphine and monoacetylmorphine (MAM) in human hair," *Fresenius' Journal of Analytical Chemistry*, 1992, 344(12):559-560.
Antignac et al., "Multi-residue extraction—purification procedure for corticosteroids in biological samples for efficient control of their misuse in livestock production," *Journal of Chromatography B*, 2001, 757:11-19.
Baumgartner, "Radioimmunoassay of Hair for Determining Opiate Abuse Histories," *J. Nucl. Med.*, 1979, 20:749-752.
'Benzodiazepines' [online]. U.S. Drug Enforcement Administration, 2008, [retrieved on Jun. 27, 2008]. Retrieved from the Internet: <URL: http://www.usdoj.gov/dea/concern/benzodiazepines.html>, 2 pages.
Cheze et al., Analytical and Practical Aspects of Drug Testing in Hair, 2007, CRC Press, pp. 163-185.
Cleland et al., "A Specific and Sensitive Assay for Disulfides," *J. of Bio. Chem*, 1968, 243(4):716-719.
Cleland, "Dithiothreitol, a New Protective Reagent for SH Groups," *Biochemistry*, 1963, 3(4):480-482.
"Dithiothreitol (DTT)," *US Biological*, 2011, 3 pages.
"DL-Dithiothreitol," *Product Information, Sigma-Aldrich*, 2011, 1 page.
"Drug Intelligence Brief, Club Drugs: An Update, Sep. 2001" [online]. U.S. Drug Enforcement Administration, 2001, [retrieved on Jun. 27, 2008]. Retrieved from the Internet (Wayback machine): <http://web.archive.org/web/20011120064344/http://www.usdoj.gov/dea/pubs/intel/01026/index.html>, 1 page.
Du et al. "Parallel Detection and Quantification Using Nine Immunoassays in a Protein Microarray for Drug from Serum Samples," *Biomed. Microdev.*, 2005, 7(2):143-146 (Abstract Only, 1 page).
Du et al., "Preparation of Steroid antibodies and parallel detection of multianabolic steroid abuse with conjugated hapten microarray," *Analyst. Chem.*, 2004, 76(20):6166-6171 (Abstract Only, 1 page).
Dunnett et al., "Retrospective Detection and Deposition Profiles of Potentiated Sulphonamides in Equine Hair by Liquid Chromatography," *Chromatographia*, 2004, 59:S69-S78.
Dunnett et al., "Trace element, toxin and drug elimination in hair with particular reference to the horse," *Res. in Vet. Science*, 2003, 75:89-101.
Gaillard et al., "Gas chromatographic-tandem mass spectrometric determination of anabolic steroids and their esters in hair: Application in doping control and meat quality control," *J. of Chroma B.*, 1999, 735(2): 189-205 (Abstract Only, 1 page).
Getz et al., "A Comparison between the Sulfhydryl Reductants Tris(2-carboxyethyl)phosphine and Dithiothreitol for Use in Protein Biochemistry," *Anal. Biochem.*, 1999, 273:73-80.

(Continued)

*Primary Examiner* — Jacob Cheu
(74) *Attorney, Agent, or Firm* — Fish & Richardson P.C.

(57) ABSTRACT

Methods that permit the rapid release of one or more analytes from head or body hair or other keratinized structures of an individual (who may previously have ingested one or more of the analytes) are provided. The methods can include contacting the keratinized structure with a reducing agent but not with a proteolytic agent. The methods can further include identification and quantification of the one or more analytes by known analytical techniques such as immunoassays. The described methods do not damage the analyte and do not cause harmful effects on a subsequently-used analyte detection probe (e.g., an antibody).

37 Claims, 2 Drawing Sheets

OTHER PUBLICATIONS

Gleixner et al., "Detection of the anabolic beta-2-adenoreceptor agonist clenbuterol in human scalp hair by HPLC/EIA," *Clin. Chem.*, 1996, 42(11):1869-1871.

Gleixner, "Examination of calf hair for effective anabolic sex steroids Meaning for residue control," *Fleischwirtschaft*, 1997, 72(12):1108-1110 English Translation, 13 pages.

Gratacos-Cubarsi et al., "Assessment of enrofloxacin and ciprofloxacin accumulation in pig and calf hair by HPLC and fluorimetric detection," *Anal and Bioanalytical Chemistry*, 2007, 387(6):1991-98.

Gratacos-Cubarsi, et al, "Traceability of sulfonamide antibiotic treatment by immunochemical analysis of farm animal hair samples," *Anal and Bioanalytical Chemistry*, 2009, 395(4):1009-16.

Gratacos-Cubarsi, et al., "Detection of sulphamethazine residues in cattle and pig hair by HPLC-DAD," *J. Chrom B*, Feb. 17, 2006, 832:121-126.

Gratacos-Cubarski et al., "Hair analysis for veterinary drug monitoring in livestock production," *J. Chromatography B*, 2006, 834:14-25.

Hernandez-Carrasquilla, "External contamination of bovine hair with $\beta_2$-agonist compounds: evaluation of decontamination strategies," *Journal of Chromatography B*, 2002, 767:235-243.

Hooijerink et al., "Liquid chromatography-electrospray ionization-mass spectrometry based method for the determination of estradiol benzoate in hair of cattle," *Analytica Chimica Acta*, 2005, 529:167-172.

Jouvel et al., "Detection of diazepam in horse hair samples by mass spectrometric methods," *Analyst*, 2000, 125:1765-1769.

Jurado, Analytical and Practical Aspects of Drug Testing in Hair, 2007, CRC Press, pp. 95-125.

Kintz et al., "Detection of Drugs in Human Hair using Abbot Adx, with confirmation by Gas Chromatography/Mass Spectrometery(GC/MS)," *Journal of Forensic Sciences*, 1992, 37(1): 328-331.

Mogos et al., "Evaluation of the metabolic balance in type 2 diabetes by assay of the hair glucose," *Rom. J. Intern. Med.*, 2003, 41:61-65.

"Morphine and 6-Monoacetylmorphine in Hair of Heroin Users: Use of Invalid Extraction Procedures Generates Erroneous Conclusions," *J. of Analytical Toxicology*, vol. 29, 2005, pp. 76-80.

Nielen et al., "Multi residue screening of intact testosterone esters and boldenone undecylenate in bovine hair using liquid chromatography electrospray tandem mass spectrometry," *J. Chromatography B*, 2006, 830:126-134.

Offidani et al., "Improved enzymatic hydrolysis of hair," *Forensic Science International*, 1993, 63:171-174.

Paisey et al., "Glycosylation of hair: possible measure of chronic hyperglycaemia," *Br. Med. J. (Clin. Res. Ed.)*, 1984, 288:669-671.

Panoyan et al., "Immunodetection of Clenbuterol in the Hair of Calves," *J. Agric. Food Chem.*,1995, 43:2716-2718 (Abstract only, 1 page).

Rambaud et al., "Study of 17β-estradiol-3-benzoate, 17α—methyltestosterone and medroxyprogesterone acetate fixation in bovine hair," *Analytica Chimica Acta*, 2005, 532:165-176.

Staub, "Analytical procedures for determination of opiates in hair: a review," *For. Sci. Int.*, 1995, 70:111-123.

Stupar et al., "Longitudinal hair chromium profiles of elderly subjects with normal glucose tolerance and type 2 diabetes mellitus," *Metabolism*, 2007, 56(1):94-104.

Suzuki et al., "Nails as useful materials for detection of methamphetamine or amphetamine abuse," *Forensic Sci. International*, 1984, 24:9-16.

Thieme et al, "Analytical strategy for detecting doping agents in hair," *Forensic Science International*, 2000, 107:335-345.

'Wikipedia' [online]. "Enzyme," 2011, [retrieved on Aug. 3, 2011]. Retrieved from the Internet: URL: < http://en.wikipedia.org/wiki/Enzyme>. 26 pages.

'Wikipedia' [online]. "Protease," 2011, [retrieved on Aug. 3, 2011]. Retrieved from the Internet: URL: <http://en.wikipedia.org/wiki/Protease>. 4 pages.

'Wikipedia' [online]. "Proteolysis," 2011, [retrieved on Aug. 3, 2011]. Retrieved from the Internet: URL: < http://en.wikipedia.org/wiki/Proteolysis>. 2 pages.

Wurst et al., "Concentration of fatty acid ethyl esters in hair of alcoholics: comparison to other biological state markers and self reported-ethanol intake," *Alcohol and Alcoholism*, 2004, 39:33-38.

Yegles et al., Analytical and Practical Aspects of Drug Testing in Hair, 2007, CRC Press, pp. 73-94.

International Search Report/Written Opinion in PCT/US09/42056 mailed Jul. 10, 2009, 13 pages.

International Search Report/Written Opinion in PCT/US09/42061 mailed Sep. 15, 2009, 18 pages.

International Search Report and Written Opinion of the International Searching Authority, PCT/US2009/042061, mailed Sep. 15, 2009, 13 pages.

International Preliminary Report on Patentability, PCT/US2009/042061, issued Nov. 2, 2010, 9 pages.

Hartmann et al., "Selective DNA attachment of micro- and nanoscale particles to substrates," *J. Mater. Res.*, 2002, 17(2):473-478.

Hongwu et al., "Parallel Detection and Quantification Using Nine Immunoassays in a Protein Microarray for Drug from Serum Samples," *Biomed. Microdev.*, 2005, 7(2):143-146.

Hongwu et al., "Preparation of Steroid antibodies and parallel detection of multianabolic steroid abuse with conjugated hapten microarray," *Analyt. Chem.*, 2004, 76(20):6166-6171.

Japanese Office Action in Japanese Application No. 2011-507600, dated Nov. 19, 2012, 15 pages.

NON-PROTEOLYTIC METHOD FOR THE DETERMINATION OF ANALYTES IN KERATINIZED STRUCTURES

CROSS-REFERENCE TO RELATED APPLICATIONS

This application is a National Stage application under 35 U.S.C. §371 and claims the benefit under 35 U.S.C. §119(a) of International Application No. PCT/US2009/042056, having an International Filing Date of Apr. 29, 2009, which claims the benefit of priority of the U.S. application Ser. No. 12/111,914, having a filing date of Apr. 29, 2008, all of which are incorporated herein in their entirety.

TECHNICAL FIELD

This disclosure relates to materials and methods for determining the presence and amount of one or more analytes of interest in keratinized structures of a subject, and more particularly to materials and methods for the same that do not require proteolytic processing of the keratinized structures.

BACKGROUND

This disclosure relates to an improved analytical method which allows the relatively rapid release and direct analysis of analytes, including organic analytes, such as certain drugs of abuse or metabolites thereof, present in hair and other keratinized structures, e.g., fingernails and toenails. The method allows for the sensitive detection of such analytes without affecting the structure of the analytes and without being detrimental to analyte probes, e.g., antibody, RNA/DNA and bio-receptor probes, which may be used to detect the analyte. For example, in some embodiments, an analyte probe can be added directly to a keratinized structure which is suspected to contain one or more analytes and which has been treated as described herein. In this way, the identity of the one or more analytes as well as the extent and duration of consumption of the one or more analytes by a subject can be evaluated.

Analysis of hair and other keratinized structures has certain advantages over urine, blood, or oral fluid analysis techniques for the detection of analytes of interest. These include ease of handling and storage, a wide window of detection, and correlation of the presence and amount of drug with time of use and ingested dose. Urine, blood, and oral fluid techniques are known to be disadvantageous in that the duration and intensity of use or exposure cannot be ascertained. These techniques can, at best, provide short term information concerning ingested analytes. In addition, there are also problems with the interpretation of such results. For example, the detection of a low level of ingested drug or drug metabolite in the urine could mean that a subject ingested a small amount of the drug very recently or a larger amount several days earlier. Thus, chronic drug use typically cannot be determined with these methods without repeated testing.

In response to the problems of establishing a reliable and accurate method that would measure both the duration and intensity of analytes of interest, work performed by Dr. Werner A. Baumgartner, as reported in "Radioimmunoassay of Hair for Determining Opiate Abuse Histories", J. Nucl Med 20:749-752 (1979), determined that long-term histories of exposure to drugs-of-abuse can be obtained through the analysis of mammalian body hair, since these substances are "trapped" within individual hair fibers during the synthesis of the fibers. In this respect, hair was shown to act like a tape recorder, i.e., past exposure histories can be evaluated through sectional analysis of hair samples. For example, it was found that morphine, once in the bloodstream, will find its way into hair as the hair is synthesized.

A variety of chemicals, including drugs-of-abuse, have been determined to be trapped by hair during its synthesis; these substances are "locked up" in hair for essentially the duration of the presence of the hair on the body. This was found to be true for head and body hair as well as for other keratinized structures such as fingernails; see Suzuki et al., Forensic Sci. International, 24:9-16, 1984. These entrapped substances cannot be washed out of hair, and were previously thought to be completely released only upon the complete, or nearly complete, destruction of the hair fiber.

Previous methods of extracting an analyte from hair included subjecting the hair to hot methanol solutions, or incubation of hair for hours (usually overnight) in an alkaline or acid medium; Yegles, et al., in: Analytical and Practical Aspects of Drug Testing in Hair, CRC Press, 2007, pp. 73-94; Jurado, C. in: Analytical and Practical Aspects of Drug Testing in Hair, CRC Press, 2007, pp. 95-125; Cheze, M. et al. in: Analytical and Practical Aspects of Drug Testing in Hair, CRC Press, 2007, pp. 163-185). Prior methods have also included the use of sonication or a mortar and pestle in conjunction with a solvent to aid in extraction.

Solvent extraction procedures can suffer from several problems in accurately determining the presence and amount of an ingested analyte. One of these problems is that the solvent extraction methods frequently remove only a small unknown and variable fraction of the total analyte present in the hair sample. Another disadvantage is that different analytes may require different solvents or different times and temperature for extraction. In addition, for analysis by immunoassay the solvents need to be evaporated, and many of the solvents are toxic and hazardous.

Other previous methods employed a combination of proteolytic and reductive treatments to completely digest and reduce the keratinized structures in order to release the one or more analytes. See, e.g., U.S. Pat. Nos. 5,466,579; 5,324,642; 6,022,693; 6,582,924; and 6,949,344, which are incorporated herein by reference, and which provide exemplary detection methods for both screening and confirmatory assays for analytes of interest, including immunoassay methods such as radioimmunassay and enzyme immunoassay methods. Such combined proteolytic and reductive treatment methods, while efficient, are relatively expensive due to the cost of the proteolytic enzyme, which can also interfere in subsequent analyte detection assays by proteolytically cleaving analyte detection probes such as antibodies, thereby preventing the use of certain highly sensitive analytical techniques or requiring the use of intermediate protease neutralization, separation, or purification steps.

Thus, there exists a need for an efficient and relatively inexpensive analyte detection method that can rapidly and completely release analytes from keratinized structures of the body such as hair, fingernails and toenails, and that can permit the direct determination of the identity of the analytes and their duration of use in a subject, without destroying or interfering with the analytes of interest and/or analyte detection probes such as immunoassay methods.

SUMMARY

Keratinized structures such as hair are complex macroassemblies of keratin polypeptide chains that are cross-linked with numerous disulfide bonds, both intramolecularly and intermolecularly, to provide the rigidity and strength of the final structure. Hair, for example, is composed of coiled-coil keratin polypeptide chains that assemble to form a "protofibril;" a number of protofibrils are then bundled in a circle around two or more protofibrils to form an multi-stranded cable known as the "microfibril;" hundreds of such microfibrils taken together result in a fibrous bundle called a "macrofibril." The macrofibrils form the cortex (or the main body) layers of the hair fiber.

An analyte of interest can be trapped in a subject's keratinized structures as these structures grow. In previous methods to detect analytes embedded in such structures, both proteolytic and reductive methods were used to fully digest and break down the keratinized structure, cleaving the keratin's proteinaceous backbone (e.g., breaking amide (peptide bond) linkages in the keratin) and reducing the intra- and intermolecular disulfide linkages to sulfhydryls, resulting in the uncoiling, unwinding, and peptidic breakage of these complex protein macrostructures. It has been surprisingly found by the present inventors that such proteolytic cleavage of the keratinized structure is not necessary to release the embedded analytes, and that treatment of the keratinized structure with a reducing agent such as Dithiothreitol ("DTT") in the absence of a proteolytic enzyme is sufficient to release the analytes in a quantitative manner as compared to previous methods. Thus, the inventors have found that the previously described synergy between a reducing agent such as DTT and a proteolytic enzyme, wherein each agent facilitated the further penetration and activity of the other agent into the hair structure, while useful, is not required to result in release of the analytes of interest. The resulting method is both cost and time effective relative to prior methods, while still providing for sensitive detection of one or more analytes of interest. Moreover, the resulting method can be used in both screening and confirmatory assays for analytes of interest and, by way of example, is also compatible with immunoassay.

Accordingly, provided herein is a method for determining the presence of an analyte in a keratinized structure sample of a subject comprising:
(a) providing an optionally washed keratinized structure sample;
(b) contacting the keratinized sample with an aqueous solution of a reducing agent, where the contacting does not proteolytically cleave the keratinized structure, to result in a test solution; and
(c) determining if the analyte is present in the test solution of step (b).

The method can further comprise determining the amount of the analyte in the test solution, if the analyte is present. In some embodiments, the method can further comprise deactivating residual reducing agent present in the test solution of step (b) prior to step (c), where the deactivating does not proteolytically cleave the keratinized structure, to result in a deactivated test solution, and determining if the analyte is present in the deactivated test solution. In some embodiments, the method can further comprise purifying the test solution of step (b) to separate the residual keratinized sample from the test solution, where the purification does not proteolytically cleave the keratinized structure, to result in a purified test solution, and determining if the analyte is present in the purified test solution.

Also provided is a method for determining the presence of an analyte in a keratinized structure sample of a subject, the method consisting essentially of:
(a) providing an optionally washed keratinized structure sample;
(b) contacting the keratinized sample with an aqueous solution of a reducing agent to result in a test solution;
(c) deactivating residual reducing agent in the test solution of (b) to result in a deactivated test solution;
(d) purifying the deactivated test solution of step (c) to remove residual keratinized sample and to result in a purified, deactivated test solution; and
(e) determining if the analyte is present in the purified, deactivated test solution of step (d). In some embodiments, the method can further comprise determining the amount of the analyte in the purified, deactivated test solution, if the analyte is present.

Also provided is a method for determining the presence of an analyte in a keratinized structure sample of a subject comprising:
(a) providing an optionally washed keratinized structure sample;
(b) contacting the keratinized sample with an aqueous solution of a reducing agent to result in a test solution; and
(c) determining if the analyte is present in the test solution, where the method does not comprise contacting the keratinized structure sample with a proteolytic enzyme. The method can further comprise determining the amount of the analyte in the test sample, if the analyte is present, and/or deactivating residual reducing agent in the test solution, and/or purifying the test solution to remove residual keratinized sample.

Further provided is a method for determining the presence of an analyte in a keratinized structure sample of a subject comprising:
(a) providing an optionally washed keratinized structure sample;
(b) contacting the keratinized sample with an aqueous solution of a reducing agent to result in a test solution; and
(c) determining if the analyte is present in the test solution, where the method does not comprise proteolytically cleaving the keratinized structure sample. The method can further comprise determining the amount of the analyte in the test sample, if the analyte is present, and/or deactivating residual reducing agent in the test solution, and/or purifying the test solution to remove residual keratinized sample.

Also provided is a method for determining the presence of an analyte in a keratinized structure sample of a subject comprising:
(a) providing an optionally washed keratinized structure sample;
(b) treating the keratinized structure sample in such a way as to reduce disulfide bonds present in the keratinized structure sample but not to cleave peptide bonds in the sample, to result in a test solution; and
(c) determining if the analyte is present in the test solution. The method can further include determining the amount of the analyte in the test sample, if the analyte is present, and/or deactivating residual reducing agent in the test solution, and/or purifying the test solution to remove residual keratinized sample.

In any of the methods described herein, the reducing agent can comprise DTT or DTE.

In any of the methods, the deactivation step can comprise contacting the test solution with an aqueous solution of a metal salt, where the metal cation of the salt is selected from the group consisting of $Cu^{++}$, $Zn^{++}$, $Mn^{++}$, $Fe^{+++}$, $Fe^{++}$, $Pb^{++}$, $Cd^{++}$, $Hg^{++}$, $Ag^{++}$, $As^{+++}$, and $Co^{++}$.

In any of the methods, the purification step can comprise separating, filtering, or centrifuging the test solution.

In any of the methods, the analyte can be determined to be present or not using an immunoassay specific for the analyte;

and in any of the methods, the immunoassay specific for the analyte can include using an antibody specific for the analyte. In some embodiments, the immunoassay is a radioimmunoassay. In some embodiments, the immunoassay is an enzyme immunoassay.

In some embodiments of the method, an analyte is determined to be present or not using a mass spectrometry technique.

In some embodiments, an analyte is determined to be present or not using a chromatographic technique.

In some embodiments of the methods, the pH at which the contacting step or treating step is performed is between about 5.0 and about 10.5, e.g., the pH at which the contacting or treating step is performed is between about 5 to about 8.8, or between about 8.8 and about 10.5.

In some embodiments of the method, the temperature at which the contacting step or treating is performed is between about 20° C. and about 40° C.

In some embodiments of the method, the contacting or treating step occurs for a time period of about 0.5 hours to about 12 hours, e.g., for a time period of about 1 to about 5 hours, or for a time period of about 2 hours.

In some embodiments, the analyte is a drug of abuse or metabolite thereof, a prescription medicine or metabolite thereof, a pain medication or metabolite thereof, a nutrient, or an endogenous analyte, or a salt form of any of the foregoing.

A drug of abuse or metabolite thereof can be selected from the group consisting of: cocaine, benzoylecgonine, cocaethylene, norcocaine, PCP, amphetamine, methamphetamine, cannabinoid, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

A keratinized structure sample can comprise hair, a fingernail, or a toenail.

In some embodiments, the keratinized structure sample, e.g., hair sample, is washed.

In some embodiments, the drug of abuse or metabolite thereof, prescription medicine or metabolite thereof, or pain medication or metabolite thereof is an opioid, cannabinoid, NSAID, steroid, amphetamine, benzodiazepine, barbiturate, tricyclic, or ephedrine, or metabolite thereof.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the presently described methods, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION

Figure 1:
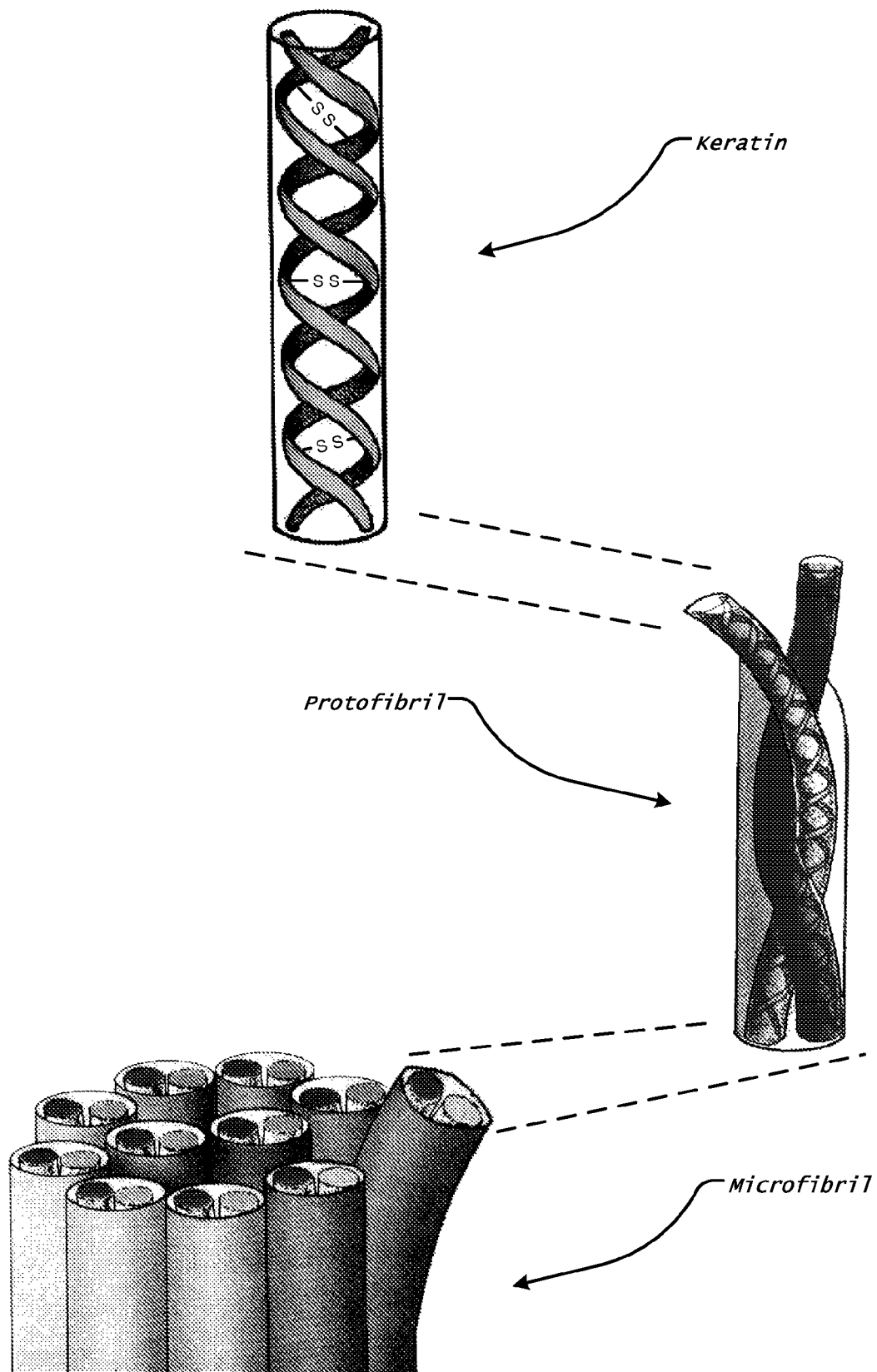
FIGS. 1 and 2 demonstrate cross-sectional views of hair to demonstrate how its complex macrostructure results from the assembly of a number of smaller structures (keratin alpha-helices; coiled-coil protofibrils, microfibrils, and macrofibrils), all of which are extensively cross-linked with disulfide bonds.
Figure 2:
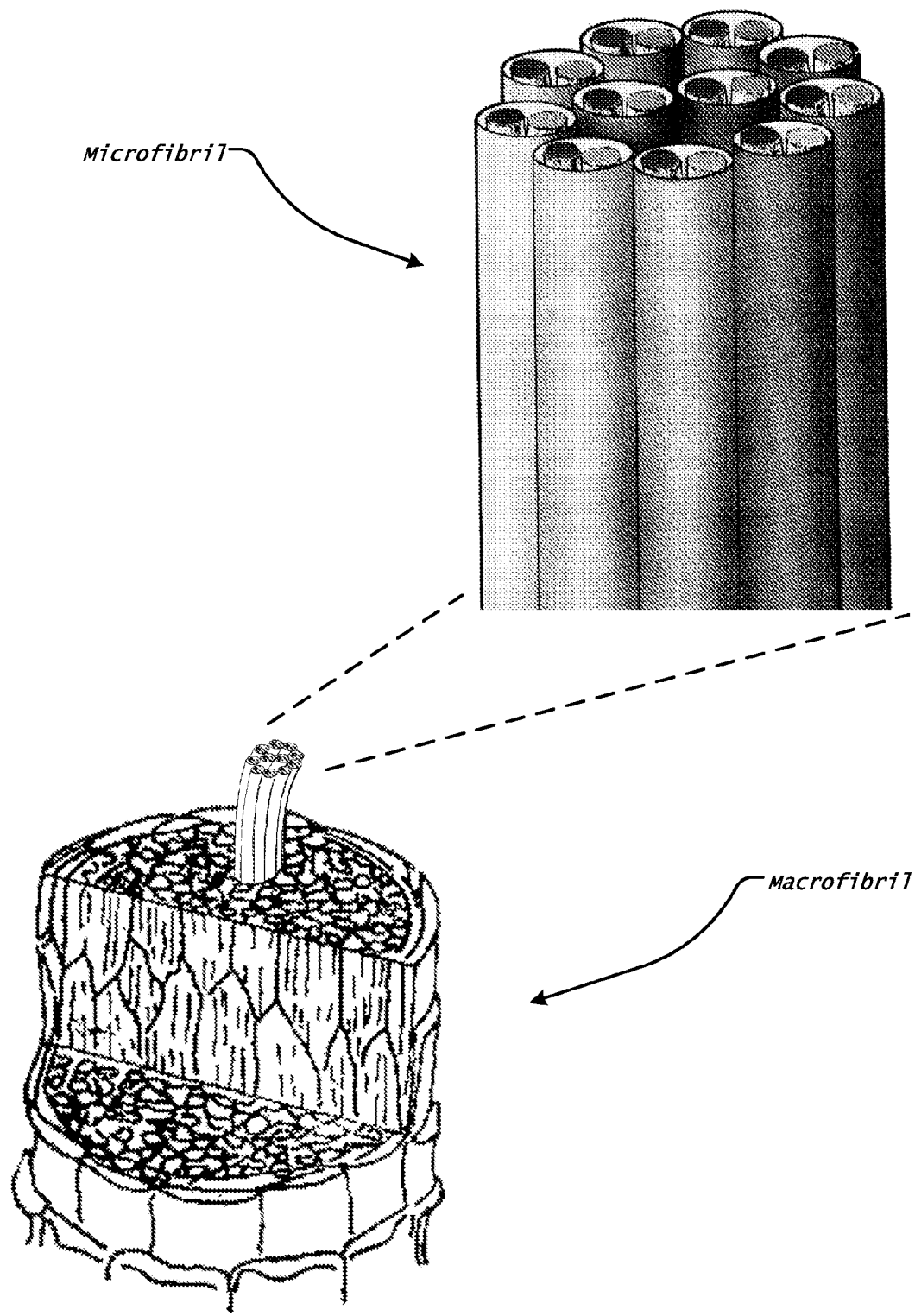

Provided herein are methods that permit the rapid release of one or more analytes from head or body hair or other keratinized structures of an individual (who previously ingested one or more of the analytes), followed by identification of the one or more analytes by known analytical techniques, including, e.g., highly sensitive receptor assays, immunoassays or instrumental techniques such as mass spectrometry or atomic absorption spectrophotometry. The release of the one or more analytes into a reducing solution from the interior of the keratinized structure occurs without damaging the analyte and without causing harmful effects on a subsequently-used analyte detection probe (e.g., an antibody). The methods also permit the detection of past use patterns in a subject over extended periods of time without performing repeated testing as is necessary in conventional testing methods which measure the content of the analyte in samples of blood, urine, or oral fluid. As previously known, the amount of analyte entrapped in hair of the same individual is directly proportional to the amount of analyte ingested, and a sectional analysis of a hair sample can provide information on historical use.

In the methods, a sample of a keratinized structure, e.g., hair, is first collected from a subject, e.g., a subject who may have ingested a particular analyte or is suspected of doing so. As used herein, the term "analyte" refers to any compound, whether endogenously produced or exogenously introduced in a subject.

Thus, in some embodiments, an analyte of interest can be exogenously introduced in the subject, i.e., not normally present in the subject, but introduced through an exogenous method, such as via inhalation, parenteral administration (e.g., IV, transdermal, subcutaneous, or IM routes), or ingestion (e.g., oral, buccal, or transmucosal routes). As used herein, a metabolite or degradation product of an exogenously introduced analyte is an exogenous analyte of interest, despite the fact that it is endogenously made in vivo in a subject, because it was derived from an exogenously introduced analyte.

In some embodiments, an analyte of interest can be an exogenously introduced drug-of-abuse, prescription medication, pain medication, organic compound, nutrient, metal, toxic chemical, pesticide, or a metabolite or degradation product thereof. Examples of drugs of abuse, pain medications, or prescription medications, or metabolites thereof, include an opioid, cannabinoid, NSAID, steroid, amphetamine, benzodiazepine, barbiturate, tricyclic, or ephedrine, or metabolite thereof.

Specific examples include: cocaine (and metabolites benzoylecgonine, cocaethylene, and norcocaine), opioids and metabolites thereof (morphine, heroin, 6-monoacetylmorphine, diacetylmorphine, codeine, oxycodone, hydrocodone, hydromorphone, oxymorphone, and methadone), cannabinoids, phencyclidine (PCP), amphetamines, methamphetamines, MDMA (ecstasy, methylenedioxy-methamphetamine), MDA (methylenedioxyamphetamine), marijuana (and THC and carboxy-THC metabolites), propoxyphene, meperidine, benzodiazepines, carisoprodol, tramadol, fentanyl, buprenorphine, naltrexone, tricyclics, nicotine (and its metabolite cotinine), eve (methylenedioxy-ethylamphetamine), flunitrazepam, lysergic acid (LSD), digoxin, methylphenidate, acetaminophen, salicylates, fluoxetine, sertraline, dextromethorphan, ephedrine, phenethylamines, pseudoephedrine, and synephrine. Pesticides include, without limitation, parathion, malathion, chlorpyrifos, diazinon, dichlorvos, and tetrachlorvinphos.

In other embodiments, an analyte of interest is endogenously produced, e.g., in an amount that correlates with the presence or absence of a disease state or metabolic state of a subject. Examples of endogenous analytes include fatty acid esters (e.g., as markers of alcohol consumption); chromium (e.g., as measure of glucose tolerance and type 2 diabetes); glucose (e.g., as measure of glucose tolerance and type 2 diabetes); and glycosyl groups (e.g., as a measure of chronic hyperglycaemia).

The keratinized sample can range in size from about 4 to about 16 mg per mL of reducing agent solution, e.g., from about 5 to about 12 mg, from about 6 to about 10 mg, from about 7 to about 15 mg, from about 5 to about 10 mg, or from about 8 to about 14 mg per mL of reducing agent solution. The sample can be first washed by known methods to remove analytes or contaminants which may have been deposited on the surface by external contact rather than by actual consumption.

The keratinized structure sample is then treated to release entrapped analytes. Importantly, the treatment method of the keratinized structure does not include contacting the keratinized structure with one or more proteolytic enzymes, such as papain, chymopapain, and proteinase K. Thus, the treatment method does not proteolytically cleave peptide (amide) bonds in the structure, e.g., not cleave them substantially. In some embodiments, the method reduces, e.g., reduces substantially, disulfide bonds present in the keratinized structure sample but does not cleave peptide bonds (e.g., does not cleave them substantially) in the sample. Typically, the treatment method comprises a reducing step, an optional deactivation step, and an optional purification (e.g., separation, filtration, or centrifugation) step.

In the reducing step, the sample is contacted with a solution of a reducing agent (reducing solution), such as Dithiothreitol ("DTT"), so as to reduce inter- and intra-molecular disulfide bonds in the keratin macrostructure, thereby releasing entrapped analyte. In some embodiments, the keratinized structure sample can be contacted with a reducing solution consisting essentially of the reducing agent, or can be contacted with a reducing solution that does not comprise a proteolytic enzyme. In some embodiments, the contacting step does not result in the substantial breakage of peptide backbone bonds (i.e., amide bonds) in the keratin polypeptide chains.

After being contacted with the reducing solution, the reduced keratinized structure sample can be optionally treated to deactivate residual reducing agent. As with the contacting step, the deactivation step is performed in the absence of a proteolytic enzyme (e.g., in a solution consisting essentially of the deactivation agent, or in a solution that does not comprise a proteolytic enzyme).

In order to determine the presence and optionally the concentration of one or more analytes, a test sample can be taken from the treated keratinized structure sample, either after the contacting step with the reducing solution or after the optional deactivation step. The sample can be removed directly, after the optional deactivation step, or after an optional purification step (e.g., separation, centrifugation, or filtration) to remove residual reduced keratinized sample.

The reducing agent for inclusion in the reducing solution can be any reducing agent capable of reducing disulfide bonds in keratinized structures. Typical examples include DTT (2,3 dihydroxybutane-1,4-dithiol) or its isomer DTE (2,3 dihydroxybutane-1,4-dithiol), thioglycolate, cysteine, sulfites, bisulfites, sulfides, bisulfides or TCEP (tris(2-carboxyethyl) phosphine), or salt forms of any of the foregoing. TCEP can be particularly useful in assays performed at lower pH ranges, e.g., 5.5 to about 8.

Typically, the concentration of the reducing agent in aqueous solution during the contacting step is about 1 to about 20 g/L, e.g., about 1 to about 15, about 2 to about 14, about 5 to about 15, about 10 to about 18, about 3 to about 12, about 4 to about 8, g/L. As one having ordinary skill in the art would recognize, the amount of reducing agent can vary based on the length of the reaction time and the detection methodology to be used.

In some embodiments, the methods may be conducted at or near room temperature and near neutral pH. For example, the method may be performed at a temperature of between about 20° C. and 60° C. (e.g., about 20, 25, 28, 30, 32, 34, 36, 38, 40, 42, 44, 46, 48, 50, 52, 54, 56, or 60° C.) and at a pH between about pH 5 and about 10.5. In some embodiments, the pH of the method is between about 8.8 and 9.7 (e.g., 8.9, 9.0, 9.1, 9.2, 9.3, 9.4, 9.45, 9.5, 9.55, 9.6, 9.65) and the method occurs at a temperature of about 37° C. In other embodiments, e.g., where an analyte of interest or metabolite or degradation product thereof is sensitive to basic pHs, a lower pH can be used, e.g., between about 5 to about 8.7 (e.g., about 5.2, 5.4, 5.6, 5.8, 6.0, 6.2, 6.4, 6.6, 7.0, 7.2, 7.4, 7.6, 7.8, 8.0, 8.2, 8.4, 8.6, or 8.7). Appropriate reaction conditions, including reaction temperature, time, and pH, can be readily determined by those having ordinary skill in the art. For additional information, see, e.g., U.S. Pat. Nos. 5,466,579; 5,324,642; 6,022, 693; 6,582,924; and 6,949,344, which are incorporated herein by reference, and which discuss methods for preserving the chemical structure of an analyte of interest (e.g., heroin metabolites, cocaine) by performing the assays at lower pHs DTT and DTE are particularly useful as reducing agents. It has been found that the use of DTT or DTE in the described processes results in release of the entrapped analytes within a relatively short period of time (depending on the amount and type of keratinized sample), e.g., in about 0.5 to about four hours, or about 1 to about 3 hours, or about 1.5 to about 2.5 hours. In certain embodiments, treatment for about 2 hours is sufficient, e.g., for about 5-15 mg of keratinized sample such as hair.

Once the one or more analytes have been released into the solution mixture, residual active reducing agent can be optionally deactivated by methods known to those having ordinary skill in the art, including simply waiting a sufficient period of time for deactivation to naturally occur. Typically this time period is from about 2 to about 14 hours after initial contact of the reducing agent with the keratinized sample, depending on the concentration and amount of reducing agent utilized, the pH, temperature, size of sample, etc.

Alternatively, as known to those having ordinary skill in the art, residual reducing agent can be deactivated with the addition of certain metal ions, typically in the form of metal salts, to the reducing solution. The addition of low amounts, e.g., from about 0.1 to about 1.0 g/L in the final sample solution, of such metal salts to the reducing solution after contacting it with the sample can significantly accelerate the time in which the reduced sample can be subjected to the analyte detection method, since it is not necessary to wait for the reducing agent to deactivate on its own. Most effective are certain metal salts which do not precipitate out of the solution after chemically linking with, and deactivating the reducing agent, such as DTT or DTE. It can be useful to avoid precipitation in the reducing solution because such precipitation could result in a loss of analyte by adsorption to the precipitate or entrapment therein, or could cause interference by particulate obstruction of optical reading methods.

In certain embodiments, precipitation is also prevented by maintaining the pH of the reducing solution from about 6 to about 8, and most preferably at about 7. One way this may be accomplished is by the addition of one molar BIS-TRIS base to keep the pH at about 7. A pH of about 7 is also a useful pH for the performance of certain analyte detection methods, such as radioimmunoassay (RIA) or enzyme immunoassay.

In addition to $Cu^{++}$ salts (e.g., copper sulfate) as described in U.S. Pat. Nos. 5,466,579 and 5,324,642, salts of $Zn^{++}$ (e.g., zinc sulfate and zinc nitrate); $Mn^{++}$ (e.g., manganese sulfate); $Fe^{+++}$ (e.g., ferric sulfate and ferric chloride); and $Fe^{++}$ (e.g., ferrous sulfate) are effective. Also effective are salts of $Pb^{++}$ (e.g., lead acetate and lead nitrate); $Cd^{++}$ (e.g., cadmium chloride); $Hg^{++}$ (e.g., mercuric chloride); $Ag^{++}$ (e.g., silver nitrate); and $Co^{++}$ (e.g., cobalt chloride). See, e.g., U.S. Pat. Nos. 6,022,693 and 6,350,582.

In certain embodiments, a salt of arsenite, such as sodium arsenite ($NaAsO_2$), may be utilized to remove residual reducing agent (e.g., DTT or DTE) by formation of a precipitable compound. Typically, 100 microliters of a 100 mg/mL solution of sodium arsenite is added to 1 mL of hair digest solution (final concentration of about 10 g/L) to effectuate the deactivation of the reducing agent. However, arsenite is not preferred because a precipitate can develop, thereby potentially adsorbing or entrapping analyte. Typically, from about 0.1 to about 1 mg (e.g., about 0.1, 0.2, 0.3, 0.4, 0.5, 0.6, 0.7, 0.8, 0.9, or 1 mg) of a metal salt in solution can be added to about 0.8 to about 1.6 mL (e.g., about 0.8, 0.9, 1.0, 1.1, 1.2, 1.3, 1.4, 1.5 or 1.6 mL) of reducing solution at a time period from about 1 to about 5 (e.g., about 1, 1.5, 2, 2.5, 3, 3.5, 4, 4.5 or 5) hours after contacting the sample with the reducing solution. Typically, the deactivation is rapidly complete, e.g., in less than about 30 minutes, such as in less than about 20 mins., less than about 10 mins., less than about 5 mins., or less than about 2 mins.

Once the treatment of the sample is complete, the reduced keratinized sample solution may be subjected to direct analysis by art recognized analyte detection methods, including receptor assays, protein-based analytical methods such as immunoassay including radioimmunoassay (RIA) or enzyme immunoassay (EIA), and/or instrumental methods such as mass spectroscopy chromatographic techniques, or atomic absorption. Thus, surprisingly it has been found that the reducing agent can destroy the disulfide linkages of keratin but not destroy the IgG proteins (antibodies) employed in an immunoassay.

In particular embodiments, instrumental methods may be used to confirm positive results obtained in immunoassay methods. Because these methods are not protein-based, the step of deactivation of reducing agent is not necessary. The speed and gentleness of the treatment method and the ability to quantitate efficiency through the inclusion of a "spike," i.e., the inclusion of a known amount of deuterated analyte, makes the presently disclosed treatment method also the method of choice for instrumental analysis methods such as gas chromatography, liquid chromatography and mass spectrometry.

The method can be used to detect the use and prior use of any analyte of interest described previously, including drugs of abuse such as cocaine, morphine/heroin and other opioids, cannabinoids, marijuana, phencyclidine or "PCP," methaqualone, and amphetamines. Moreover, the method can be effective in determining prior usage of prescription drugs such as digoxin, methadone and benzodiazepines. It is contemplated that any analyte, particularly any organic analyte, present in the bloodstream of an individual which is transferred to the hair during its synthesis can be extracted and analyzed in accordance with the methods described herein.

In certain embodiments a detergent can be used to aid in the release of one or more analytes of interest. Certain biological detergent compounds useful for solubilizing biological membrane components aid in the release of the analytes at a relatively low pH while not interfering with reduction or subsequent analyte detection. These biological detergents can aid the in the treatment of a keratinized sample at a pH in the range of about 5 to about 10.5. Suitable detergents include bile acid detergents, such as glycocholic acid, cholic acid, taurocholic acid, deoxycholic acid, glycodeoxycholic acid, taurodeoxycholic acid and salts thereof, including sodium salts. Other detergents for use in the methods are sulfo-betaines, such as the Zwittergents® and betaines, such as Empigen BB (N-dodecyl-N,N-dimethylglycine) (all available from Calbiochem Corp., La Jolla, Calif.). Other detergents include alkylglucosides, including hexyl-beta-D-glucopyranoside, heptyl-beta-D-glucopyranoside, octyl-beta-D-glucopyranoside, nonyl-beta-D-glucopyranoside, decyl-beta-D-glucopyranoside, dodecyl-beta-D-maltoside and octyl-beta-D-thioglucopyranoside (OSGP). Mixtures of alkylglucosides, such as the product ELUGENT® (Calbiochem), are also effective.

Particularly preferred are the bile acids cholic acid and glycocholic acid, which aid in the digestion of hair at a pH in the range of about 6.3 to about 8. The deoxycholates such as deoxycholic acid and glycodeoxycholic acid are effective in aiding in the digestion of hair at a pH above about 7.

The detergents can be used in the industry standard five-drug screen for the most common drugs of abuse in the United States, i.e., marijuana, cocaine, phencyclidine, methamphetamine and opioids, measured using the methods described herein. Thus, they do not impact any of the analytes or antibodies involved in the five-drug screen, and do not result in false negatives or positives. The particular detergents most effective for use in the five-drug screen are cholate, deoxycholate, cholic acid, deoxycholic acid, octyl-beta-D-glucopyranoside and octyl-beta-D-thioglucopyranoside. The bile acid detergents, alkylglucosides, sulfobetaines and betaines are preferred when a screen is performed that includes cocaine, opioids, phencyclidine, amphetamines and sympathomimetic amines. In a screen solely for cocaine, the preferred detergents are cholic acid, Zwittergents®, alkylglucoides, and N-dodecyl-N,N dimethylglycine.

In practice, the biological detergent is mixed with the aqueous reducing solution prior to contact of the solution with the keratinized sample at a temperature range of about 30 to about 40° C. Typically, about 1-2 mg of biological detergent is added to about 1 ml of reducing solution.

Additional information on the methods described herein, including the use of biological detergents, ion exchange resins (e.g., to remove interfering substances), and varying pH ranges for digestion, can be found in U.S. Pat. Nos. 6,022,693 and 6,350,582, incorporated herein by reference.

The benefits to be obtained from the presently disclosed methods are many, including a prompt, accurate, and inexpensive determination of prior exposure to a particular analyte. The method can provide a record of consumption, or non-consumption, over very long periods of time. By removal of any proteolytic treatment steps, both the expense of a proteolytic method and certain interferences with biological analyte detection agents are reduced. Surprisingly, a synergistic interaction between a proteolytic enzyme and a reducing agent for diffusion of each agent into the hair structure is not required for efficient release of analytes of interest. Moreover, hair collection is less intrusive and less physically repulsive than blood or urine collection, and samples cannot be altered or substituted, nor can detection be evaded by short term abstention or "flushing" (excessive fluid intake) prior to a scheduled testing, e.g., pre-employment test or annual physical examination. Samples may be stored indefinitely without refrigeration. Finally, the methods facilitate both screening and confirmatory assays for detecting an analyte of interest.

The following examples are meant to be illustrative and do not limit the claims.

EXAMPLES

Example I

Radioimmunoassays of Nonproteolytic Digests of Hair Samples

To 8 mg of hair samples in test tubes 1.6 mL of 6% Diththiothreitol (pH 9.5) was added and the samples incubated at 37° C. for 2 hours. The samples were then neutralized with 140 uL of 1.0 M Bis Tris (pH 7) containing 6% Copper Sulfate Pentahydrate, mixed, and centrifuged. Supernatants were sampled to be assayed for Cocaine, Opioids, PCP, Amphetamines, and Cannabinoids.

The radioimmunoassays were performed by combining aliquots of sample with $I^{125}$-labeled drug and a primary antibody directed against the drug. The labeled and unlabeled drug in the sample compete for binding sites on the primary antibody. After incubation, a second antibody directed against the primary antibody was added to precipitate the antibody-bound drug. After centrifugation and decanting of the liquid superantants, the precipitated bound fractions were counted in a gamma counter.

Example Cocaine Results

|  | Percent | Comparative RIA result* | MS Results--on washed samples; ng/10 mg hair** | | | |
|---|---|---|---|---|---|---|
|  |  |  | COC | BE | CE | NOR |
| NEGATIVE (Bo) | 100 |  |  |  |  |  |
| Cutoff (5 ng/10 mg hair) | 53.9 |  |  |  |  |  |
| Pos Sample 59498 | 12.5 | 12 | 31.6 | 13 | 6.3 | 1.1 |
| Pos Sample 59501 | 22.3 | 23 | 12.7 | 0.7 | 0 | 0 |
| Pos Sample 59571 | 27.8 | 29 | 9.4 | 1.3 | 0 | 0.3 |
| Neg Sample 59718 | 97.5 | 97.4 |  |  |  |  |
| Neg Sample 59708 | 91.3 | 94.9 |  |  |  |  |
| Neg Sample 58714 | 94.6 | 94.5 |  |  |  |  |
| minus 50% control (2.5 ng/10 mg hair) | 61.5 |  |  |  |  |  |
| plus 50% control (7.5 ng/10 mg hair) | 44 |  |  |  |  |  |

*Comparative RIA result using methods described in U.S. Pat. Nos.; 5,324,642 and 6,350,582.
**MS = mass spectrometric quantitation of drug present in sample.
COC = cocaine;
BE = benzoylecgonine;
CE = cocaethylene;
NOR = norcocaine Note: Explanation of Percent B/Bo for the RIA assays—The Negative (Bo) value of 100% is the value for the reference tube containing no analyte in the sample and exhibits maximum binding of antibody to radioactive tracer. Unknown samples are expressed as percent of the Negative Bo, termed "Percent B/Bo." Concentrations of analyte in the samples vary inversely with Percent B/Bo values. A positive sample is one containing drug equal to or more than the cutoff calibrator and thus a Percent B/Bo equal to or lower than the cutoff calibrator.

Example Opioid Results

|  | Percent | Comparative RIA result* | MS Results--on washed samples; ng/10 mg hair** | | | |
|---|---|---|---|---|---|---|
|  |  |  | Codeine | Morphine | MAM | Oxycodone |
| NEGATIVE (Bo) | 100 |  |  |  |  |  |
| Cutoff (2 ng/10 mg hair) | 65 |  |  |  |  |  |
| Pos Sample 59028 | 30.1 | 32.8 | 0.8 | 7.9 | 7.8 | 0.3 |
| Pos Sample 58641 | 15.7 | 9.6 | 3.6 | 48.8 | 85.4 | 0.8 |
| Pos Sample 58714 | 24.3 | 23.6 | 4.3 | 21.3 | 5.4 | 0 |
| Neg Sample 59051 | 92.8 | 96 |  |  |  |  |
| Neg Sample 59498 | 98.2 | 98.2 |  |  |  |  |
| Neg Sample 53429 | 93.6 | 92.5 |  |  |  |  |
| minus 50% control (1 ng/10 mg hair) | 72.9 |  |  |  |  |  |
| plus 50% control (3 ng/10 mg hair) | 53.8 |  |  |  |  |  |

*Comparative RIA result using methods described in U.S. Pat. Nos. 5,324,642 and 6,350,582.
**MS = mass spectrometric quantitation of drug present in sample.
MAM = 6-monoacetylmorphine

Example Results for PCP

|  | Percent | Comparative RIA result* | MS Results--on washed samples** PCP |
|---|---|---|---|
| NEGATIVE (Bo) | 100 |  | ng/10 mg hair |
| Cutoff (3 ng/10 mg hair) | 59 |  |  |
| Pos Sample 53155 | 20.2 | 21.6 | 22.4 |
| Pos Sample 53429 | 17.5 | 20.1 | 22.6 |
| Pos Sample 53151 | 28.9 | 25.8 | 7.6 |
| Neg Sample 59718 | 97.3 |  |  |
| Neg Sample 59740 | 95.7 |  |  |
| Neg Sample 59666 | 95.5 |  |  |
| minus 50% control (1.5 ng/10 mg hair) | 72.9 |  |  |
| plus 50% control (4.5 ng/10 mg hair) | 49.4 |  |  |

*Comparative RIA result using methods described in U.S. Pat. Nos. 5,324,642 and 6,350,582.
**MS = mass spectrometric quantitation of drug present in sample. PCP = phencyclidine

Example Results for Amphetamines

|  | Percent | Comparative RIA result* | MS Results--on washed samples; ng/10 mg hair** | | | | |
|---|---|---|---|---|---|---|---|
|  |  |  | METH | AMP | MDMA | MDA | MDEA |
| NEGATIVE (Bo) | 100 |  |  |  |  |  |  |
| Cutoff (5 ng/10 mg hair) | 56.4 |  |  |  |  |  |  |
| Pos Sample 59708 | 8.1 | 8.9 | 2.6 | 0 | 214 | 6.7 | 0 |
| Pos Sample 59714 | 16.5 | 15.4 | 26.9 | 3.8 | 0 | 0 | 0 |

-continued

|  | Percent | Comparative RIA result* | MS Results--on washed samples; ng/10 mg hair** | | | | |
|---|---|---|---|---|---|---|---|
|  |  |  | METH | AMP | MDMA | MDA | MDEA |
| Pos Sample 59718 | 36.6 | 55.5 | 6.7 | 0.7 | 0 | 0 | 0 |
| Neg Sample 59501 | 93.1 | 96.8 |  |  |  |  |  |
| Neg Sample 59571 | 90.8 | 90 |  |  |  |  |  |
| Neg Sample 59028 | 95.8 | 94.9 |  |  |  |  |  |
| minus 50% control (2.5 ng/10 mg hair) | 60.3 |  |  |  |  |  |  |
| plus 50% control (7.5 ng/10 mg hair) | 47.4 |  |  |  |  |  |  |

*Comparative RIA result using methods described in U.S. Pat. Nos. 5,324,642 and 6,350,582.
**MS = mass spectrometric quantitation of drug present in sample.
METH = methamphetamine;
AMP = amphetamine;
MDA = 3,4-methylenedioxyamphetamine;
MDMA = 3,4-methylenedioxymethamphetamine

Example II

Enzyme Immunoassays of Non-Proteolytic Digests of Hair Samples Using Commercially Available Antibody-Coated Microplates To 8 mg of hair samples in test tubes 0.8 mL of 1.5% Diththiothreitol (pH 9.5) was added and the samples incubated at 37° C. for 2 hours. The samples were then neutralized with 70 uL of 1.0 Bis-Tris (pH 7) containing 1.25% Zinc, mixed, and centrifuged. Supernatants were sampled to be assayed for PCP (phencyclidine) on an antibody-coated microplate. After 1 hour incubation of sample in the wells, the wells were emptied and washed once prior to addition of HRP-antigen and continuation of the method described by the vendor (Cozart Industries).

Example Results for PCP

|  | Percent | MS Results** PCP ng/10 mg hair |
|---|---|---|
| NEGATIVE (Bo) | 100 |  |
| Cutoff (3 ng/10 mg hair) | 63.0 |  |
| Pos Sample 53155 | 51.1 | 22.4 |
| Pos Sample 53429 | 53.6 | 22.6 |
| Pos Sample 53151 | 55.2 | 7.6 |
| Neg Sample 42647 | 101.1 |  |
| Neg Sample 42650 | 99.4 |  |
| Neg Sample 42665 | 99.8 |  |
| Neg Sample 42677 | 101.6 |  |
| minus 50% control (1.5 ng/10 mg hair) | 78.6 |  |
| plus 100% control (6 ng/10 mg hair) | 53.2 |  |

**MS = mass spectrometric quantitation of drug present in sample. PCP = phencyclidine

Example III

Instrumental Analysis of Low-pH Non-Proteolytic Digestion of Hair Samples

To 12 mg of hair in test tubes was added 1.2 mL of a 1.0 M Bis-Tris solution (pH 5.5) containing 12% Dithiothreitol and 0.2% Cholic Acid. Samples are incubated overnight (8-12 hours) at 37° C. with shaking at 120 oscillations/minute. Supernatants from these digested samples are analyzed after clean-up/extraction for subsequent analytical procedures (e.g., MS).

Example IV

Demonstration that the Reducing Agent (e.g., DTT) is the Active Ingredient in the Digests To demonstrate that DTT is the active ingredient in the presently described non-proteloytic digestion methods, an aliquot of a codeine-positive hair sample was contacted with a Tris-buffered solution at pH 9.5 (containing no DTT), and another aliquot of the sample was contacted solution at pH 9.5 containing 6 grams DTT/L. The pH 9.5 solution without DTT recovered 2.36 ng of codeine per 10 mg hair, while the pH 9.5 solution containing DTT recovered 19.34 ng codeine per 10 mg hair.

Other Embodiments

A number of embodiments have been described. Nevertheless, it will be understood that various modifications may be made without departing from the spirit and scope of the disclosure provided herein. Accordingly, other embodiments are within the scope of the following claims.

What is claimed is:
1. A method for determining the presence of an analyte in a keratinized structure sample of a subject comprising:
  (a) providing an optionally washed keratinized structure sample;
  (b) contacting the keratinized sample with an aqueous solution of a reducing agent comprising dithiothreitol (DTT), dithioerythritol (DTE), or a mixture thereof to result in a test solution, wherein said contacting does not proteolytically cleave the keratinized structure and wherein the contacting step is performed at a pH from about 7.0 to about 10.5; and
  (c) determining if the analyte is present in the test solution of step (b).
2. The method of claim 1, further comprising determining the amount of the analyte in the test solution, if the analyte is present.
3. The method of claim 1, further comprising deactivating residual reducing agent present in the test solution of step (b) prior to step (c), wherein said deactivating does not pro- teolytically cleave the keratinized structure, to result in a deactivated test solution, and determining if the analyte is present in the deactivated test solution.

4. The method of claim 1, further comprising purifying the test solution of step (b) to separate the residual keratinized sample from the test solution, wherein said purification does not proteolytically cleave the keratinized structure, to result in a purified test solution, and determining if the analyte is present in the purified test solution.

5. A method for determining the presence of an analyte in a keratinized structure sample of a subject, the method consisting essentially of:
(a) providing an optionally washed keratinized structure sample;
(b) contacting the keratinized sample with an aqueous solution of a reducing agent comprising dithiothreitol (DTT), dithioerythiritol (DTE), or a mixture thereof to result in a test solution, wherein the contacting step is performed at a pH from about 7.0 to about 10.5;
(c) deactivating residual reducing agent in the test solution of (b) to result in a deactivated test solution;
(d) purifying the deactivated test solution of step (c) to remove residual keratinized sample and to result in a purified, deactivated test solution; and
(e) determining if the analyte is present in the purified, deactivated test solution of step (d).

6. The method of claim 5, further comprising determining the amount of the analyte in the purified, deactivated test solution, if the analyte is present.

7. A method for determining the presence of an analyte in a keratinized structure sample of a subject comprising:
(a) providing an optionally washed keratinized structure sample;
(b) contacting the keratinized sample with an aqueous solution of a reducing agent comprising dithiothreitol (DTT), dithioerythiritol (DTE), or a mixture thereof to result in a test solution, wherein the contacting step is performed at a pH from about 7.0 to about 10.5; and
(c) determining if the analyte is present in the test solution, wherein the method does not comprise contacting the keratinized structure sample with a proteolytic enzyme.

8. The method of claim 7, further comprising determining the amount of the analyte in the test sample, if the analyte is present.

9. The method of claim 7, further comprising deactivating residual reducing agent in the test solution.

10. The method of claim 7, further comprising purifying the test solution to remove residual keratinized sample.

11. A method for determining the presence of an analyte in a keratinized structure sample of a subject comprising:
(a) providing an optionally washed keratinized structure sample;
(b) contacting the keratinized sample with an aqueous solution of a reducing agent comprising dithiothreitol (DTT), dithioerythiritol (DTE), or a mixture thereof to result in a test solution, wherein the contacting step is performed at a pH from about 7.0 to about 10.5; and
(c) determining if the analyte is present in the test solution, wherein the method does not comprise proteolytically cleaving the keratinized structure sample.

12. The method of claim 11, further comprising determining the amount of the analyte in the test sample, if the analyte is present.

13. The method of claim 11, further comprising deactivating residual reducing agent in the test solution.

14. The method of claim 11, further comprising purifying the test solution to remove residual keratinized sample.

15. A method for determining the presence of an analyte in a keratinized structure sample of a subject comprising:
(a) providing an optionally washed keratinized structure sample;
(b) treating the keratinized structure sample with a reducing agent comprising dithiothreitol (DTT), dithioerythiritol (DTE), or a mixture thereof in such a way as to reduce disulfide bonds present in the keratinized structure sample but not to cleave peptide bonds in the sample, to result in a test solution, wherein the treating is performed at a pH from about 7.0 to about 10.5; and
(c) determining if the analyte is present in the test solution.

16. The method of claim 15, further comprising determining the amount of the analyte in the test sample, if the analyte is present.

17. The method of any of claim 3, 5, 9, or 13, wherein the deactivation step comprises contacting the test solution with an aqueous solution of a metal salt, wherein the metal cation of the salt is selected from the group consisting of $Cu^{++}$, $Zn^{++}$, $Mn^{++}$, $Fe^{+++}$, $Fe^{++}$, $Pb^{++}$, $Ca^{++}$, $Hg^{++}$, $Ag^{++}$, $As^{+++}$, and $Co^{++}$.

18. The method of any of claim 4, 5, 10, or 14, wherein the purification step comprises separating, filtering, or centrifuging the test solution.

19. The method of any of claim 1, 5, 7, 11, or 15, wherein the analyte is determined to be present or not using an immunoassay specific for the analyte.

20. The method of claim 19, wherein the immunoassay specific for the analyte comprises using an antibody specific for the analyte.

21. The method of claim 19, wherein the immunoassay is a radioimmunoassay.

22. The method of claim 19, wherein the immunoassay is an enzyme immunoassay.

23. The method of any of claim 1, 5, 7, 11, or 15, wherein the analyte is determined to be present or not using a mass spectrometry technique.

24. The method of any of claim 1, 5, 7, 11, or 15, wherein the analyte is determined to be present or not using a chromatographic technique.

25. The method according to any one of claim 1, 5, 7, 11, or 15, wherein the pH at which the contacting or treating step is performed is between about 8.8 and about 10.5.

26. The method according to any of claim 1, 5, 7, 11, or 15, wherein the temperature at which the contacting step or treating is performed is between about 20° C. and about 40° C.

27. The method according to any of claim 1, 5, 7, 11, or 15, wherein the contacting or treating step occurs for a time period of about 0.5 hours to about 12 hours.

28. The method according to claim 27, wherein the contacting or treating step occurs for a time period of about 1 to about 5 hours.

29. The method of claim 27, wherein the contacting or treating step occurs for a time period of about 2 hours.

30. The method of any of claim 1, 5, 7, 11, or 15, wherein the analyte is a drug of abuse or metabolite thereof, a prescription medicine or metabolite thereof, a pain medication or metabolite thereof, a nutrient, or an endogenous analyte, or a salt form of any of the foregoing.

31. The method of claim 30, wherein the drug of abuse or metabolite thereof is selected from the group consisting of: cocaine, benzoylecgonine, cocaethylene, norcocaine, PCP, amphetamine, methamphetamine, cannabinoid, THC, carboxy-THC, heroin, codeine, morphine, 6-monoacetylmorphine (MAM), oxycodone, 3,4-methylenedioxyamphetamine (MDA); and 3,4-methylenedioxymethamphetamine (MDMA).

32. The method according to any of claim 1, 5, 7, 11, or 15, wherein the keratinized structure sample comprises hair, a fingernail, or a toenail.

33. The method of claim 32, wherein the keratinized structure sample comprises hair.

34. The method according to any of claim 1, 5, 7, 11, or 15, wherein the keratinized structure comprises hair and the hair sample is washed.

35. The method of claim 15, further comprising deactivating residual reducing agent in the test solution.

36. The method of claim 15, further comprising purifying the test solution to remove residual keratinized sample.

37. The method of claim 30, wherein the drug of abuse or metabolite thereof, prescription medicine or metabolite thereof, or pain medication or metabolite thereof is an opioid, cannabinoid, NSAID, steroid, amphetamine, benzodiazepine, barbiturate, tricyclic, or ephedrine, or metabolite thereof.

* * * * *

UNITED STATES PATENT AND TRADEMARK OFFICE
CERTIFICATE OF CORRECTION

| | | |
|---|---|---|
| PATENT NO. | : 8,435,747 B2 | Page 1 of 1 |
| APPLICATION NO. | : 12/990447 | |
| DATED | : May 7, 2013 | |
| INVENTOR(S) | : Virginia Hill | |

It is certified that error appears in the above-identified patent and that said Letters Patent is hereby corrected as shown below:

Title Page, Item (45) Date of Patent:, please insert --*-- before May 7, 2013, therefor;

Title Page, please insert Item --Related U.S. Application Data,
    (63) This application is a 371 of PCT/US09/42056, filed April 29, 2009, which is a continuation of application No. 12/111,914, filed April 29, 2008, now Pat. No. 8,084,215--, therefor;

Title Page 2, Column 2 Item (56) (Other Publications), please delete "estradio1" and insert --estradiol--, therefor;

In the Claims

Column 15, line 17 (Claim 5), please delete "dithioerythiritol (DTE)," and insert --dithioerythritol (DTE),--, therefor;

Column 15, line 36 (Claim 7), please delete "dithioerythiritol (DTE)," and insert --dithioerythritol (DTE),--, therefor;

Column 15, line 55 (Claim 11), please delete "dithioerythiritol (DTE)," and insert --dithioerythritol (DTE),--, therefor;

Column 16, lines 6-7 (Claim 15), please delete "dithioerythiritol (DTE)," and insert --dithioerythritol (DTE),--, therefor;

Column 16, line 21 (Claim 17), please delete "$Ca^{++}$," and insert --$Cd^{++}$,--, therefor;

Column 16, line 46 (Claim 26), please delete "20° C.", and insert --20° C--, therefor.

Signed and Sealed this
Eighteenth Day of November, 2014

Michelle K. Lee
*Deputy Director of the United States Patent and Trademark Office*